United States Patent
Elrayes et al.

(10) Patent No.: US 10,792,321 B1
(45) Date of Patent: Oct. 6, 2020

(54) MASSAGE AND SPORT CREAM COMPOSITION SYSTEMS

(71) Applicants: Nermeen Samir Elrayes, Sugarland, TX (US); Samir S. H. Alrayyes, Jeddah (SA); Shdia A. S. Alrayyes, Jeddah (SA); Lina S. S. Alrayyes, Jeddah (SA); Lana S. S. Alrayyes, Jeddah (SA); Bodour Samir Shaban Alrayyes, Jeddah (SA); Bader S. S. Alrayyes, Jeddah (SA); Mohammed S. S. Alrayyes, Jeddah (SA); Nevin S. S. Doshan, Abu Dhabi (AE)

(72) Inventors: Nermeen Samir Elrayes, Sugarland, TX (US); Samir S. H. Alrayyes, Jeddah (SA); Shdia A. S. Alrayyes, Jeddah (SA); Lina S. S. Alrayyes, Jeddah (SA); Lana S. S. Alrayyes, Jeddah (SA); Bodour Samir Shaban Alrayyes, Jeddah (SA); Bader S. S. Alrayyes, Jeddah (SA); Mohammed S. S. Alrayyes, Jeddah (SA); Nevin S. S. Doshan, Abu Dhabi (AE)

( * ) Notice: Subject to any disclaimer, the term of this patent is extended or adjusted under 35 U.S.C. 154(b) by 179 days.

(21) Appl. No.: 16/136,245

(22) Filed: Sep. 19, 2018

Related U.S. Application Data

(62) Division of application No. 15/591,713, filed on May 10, 2017, now abandoned.

(60) Provisional application No. 62/399,719, filed on Sep. 26, 2016.

(51) Int. Cl.
| | | |
|---|---|---|
| *A61K 36/00* | (2006.01) | |
| *A61K 36/47* | (2006.01) | |
| *A61K 47/20* | (2006.01) | |
| *A61K 47/02* | (2006.01) | |
| *A61K 47/22* | (2006.01) | |
| *A61K 9/06* | (2006.01) | |
| *A61K 9/00* | (2006.01) | |
| *A61K 47/44* | (2017.01) | |
| *A61K 36/899* | (2006.01) | |
| *A61K 47/14* | (2017.01) | |
| *A61K 47/10* | (2017.01) | |
| *A61P 25/00* | (2006.01) | |

(52) U.S. Cl.
CPC ............ *A61K 36/47* (2013.01); *A61K 9/0014* (2013.01); *A61K 9/06* (2013.01); *A61K 36/899* (2013.01); *A61K 47/02* (2013.01); *A61K 47/10* (2013.01); *A61K 47/14* (2013.01); *A61K 47/20* (2013.01); *A61K 47/22* (2013.01); *A61K 47/44* (2013.01); *A61P 25/00* (2018.01)

(58) Field of Classification Search
CPC ..................................................... A61K 36/00
USPC .......................................................... 424/725
See application file for complete search history.

(56) References Cited

U.S. PATENT DOCUMENTS 7,368,135 B1    5/2008  Anderson

*Primary Examiner* — Michael V Meller
(74) *Attorney, Agent, or Firm* — Charles Runyan

(57) ABSTRACT

A cream composition for massage and sport is disclosed herein. The cream composition includes ricinus communis (castor) seeds oil, sesamum indicum (sesame) seeds oil, deionized water, isopropyl myristate, triticum vulgare (wheat) germ oil, butyrospermum parkii (shea) butter, white iodine, cetostearyl alcohol, a fragrance, sodium laureth sulfate (SLES), bentonite, dmdm hydantoin, sodium chloride, benzyl alcohol, and behydroacetic acid. The composition is administered topically to assist with comforting muscular pain, increasing flexibility, and improving overall skin health.

1 Claim, 4 Drawing Sheets

MASSAGE AND SPORT CREAM COMPOSITION SYSTEMS

CROSS-REFERENCE TO RELATED APPLICATION

The present application is related to and claims priority to U.S. Provisional Patent Application No. 62/399,719, filed Sep. 26, 2016, which is incorporated by reference herein in its entirety.

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

1. Field of the Invention

The present invention relates generally to the field of topical creams and more specifically relates to cream compositions for massage and sport.

2. Description of Related Art

Millions of individuals suffer from acute or chronic pain every year. In 2012, a study by health economists from Johns Hopkins University estimated the total cost of chronic pain in the United States to be well over 600 billion annually. The Johns Hopkins study highlights the staggering impact of acute and chronic pain on a nation's health-care system, work productivity, and health insurance costs. Beyond the measurable economic impacts, the human suffering associated with pain is incalculable.

There are primarily three types of pain: somatic, visceral, and neuropathic, which can be acute and chronic. Somatic pain is caused by the activation of pain receptors in either the cutaneous or musculoskeletal tissues. In contrast to surface somatic pain, which is usually described as sharp and may have a burning or pricking quality, deep somatic pain is usually characterized as a dull, aching but localized sensation. Somatic pain may include fractures in the vertebrae, joint pain (deep somatic pain) and postsurgical pain from a surgical incision (surface pain). Inflammatory pain shares elements in common with somatic, visceral and neuropathic pain since these conditions can induce inflammatory events. Inflammatory pain is related to tissue damage which can occur in the form of penetration wounds, burns, extreme cold, fractures, inflammatory arthropathies, as seen in many autoimmune conditions, excessive stretching, infections, vasoconstriction, and cancer.

Conventional treatments for pain include the prescribing of pharmacologic analgesics such as acetaminophen, NSAIDs such as Ibuprofen, cyclooxygenase 2 (COX-2) inhibitors, and synthetic opioids (narcotic painkillers) such as codeine, oxycodone, and the like. It is well known that these drugs are poorly tolerated by many individuals, and carry with their use substantial risks, particularly in pregnant patients, elderly patients, and individuals with certain pre-existing conditions. As examples, acetaminophen can be toxic to patients with liver disease, long-term NSAID use has been associated with gastric disorders, and narcotic painkillers can produce a myriad of serious side effects including respiratory depression, nausea, and chemical addiction. For the reasons stated above, it is clear that alternatives to conventional drug therapies, and the risks associated with their use, would be of great benefit to many who suffer from acute or chronic pain.

U.S. Pat. No. 7,368,135 to Anderson relates to an "Herbal healing oil." The described herbal healing oil includes a chemical formula for the composition of a liquid topical analgesic that comprises at least olive oil, castor oil, grapeseed oil, almond oil, apricot kernel oil, Vitamin E, various herbal essential oils, and a stabilizer. Alternate and additional essential oils or plant- and/or vegetable-derived oils are anticipated to be used as well. When produced, the mixture would be bottled and promoted to the public to be used as a topical rubbing compound for the skin or for use in a soaking bath. It will reduce pain from sore muscles, bruised ligaments and tendons, lower back pain, arthritis and other similar ailments associated with common aches and pains.

BRIEF SUMMARY OF THE INVENTION

In view of the foregoing disadvantages inherent in the known cream compositions for massage and sport art, the present disclosure provides a novel massage and sport cream composition. The general purpose of the present disclosure, which will be described subsequently in greater detail, is to assist with muscular comfort, increasing flexibility, and improving overall skin health. Further, the present disclosure may assist with comforting muscular pain, swelling, fatigue, cramps, increasing flexibility and mobility, easing joint pain and nerve pain.

A cream composition for massage and sport is disclosed herein. The cream composition for massage and sport includes ricinus communis (castor) seeds oil, sesamum indicum (sesame) seeds oil, deionized water, isopropyl myristate, triticum vulgare (wheat) germ oil, butyrospermum parkii (shea) butter, white iodine, cetostearyl alcohol, a fragrance, sodium laureth sulfate (SLES), bentonite, dmdm hydantoin, sodium chloride, benzyl alcohol, and behydroacetic acid.

For purposes of summarizing the disclosure, certain aspects, advantages, and novel features of the disclosure have been described herein. It is to be understood that not necessarily all such advantages may be achieved in accordance with any one particular embodiment of the disclosure. Thus, the disclosure may be embodied or carried out in a manner that achieves or optimizes one advantage or group of advantages as taught herein without necessarily achieving other advantages as may be taught or suggested herein. The features of the disclosure which are believed to be novel are particularly pointed out and distinctly claimed in the concluding portion of the specification. These and other features, aspects, and advantages of the present disclosure will become better understood with reference to the following drawings and detailed description.

BRIEF DESCRIPTION OF THE DRAWINGS

The figures which accompany the written portion of this specification illustrate embodiments and methods of use for the present disclosure, a massage and sport cream composition system, constructed and operative according to the teachings of the present disclosure.

The various embodiments of the present disclosure will hereinafter be described in conjunction with the appended drawings, wherein like designations denote like elements.

DETAILED DESCRIPTION

Figure 1:
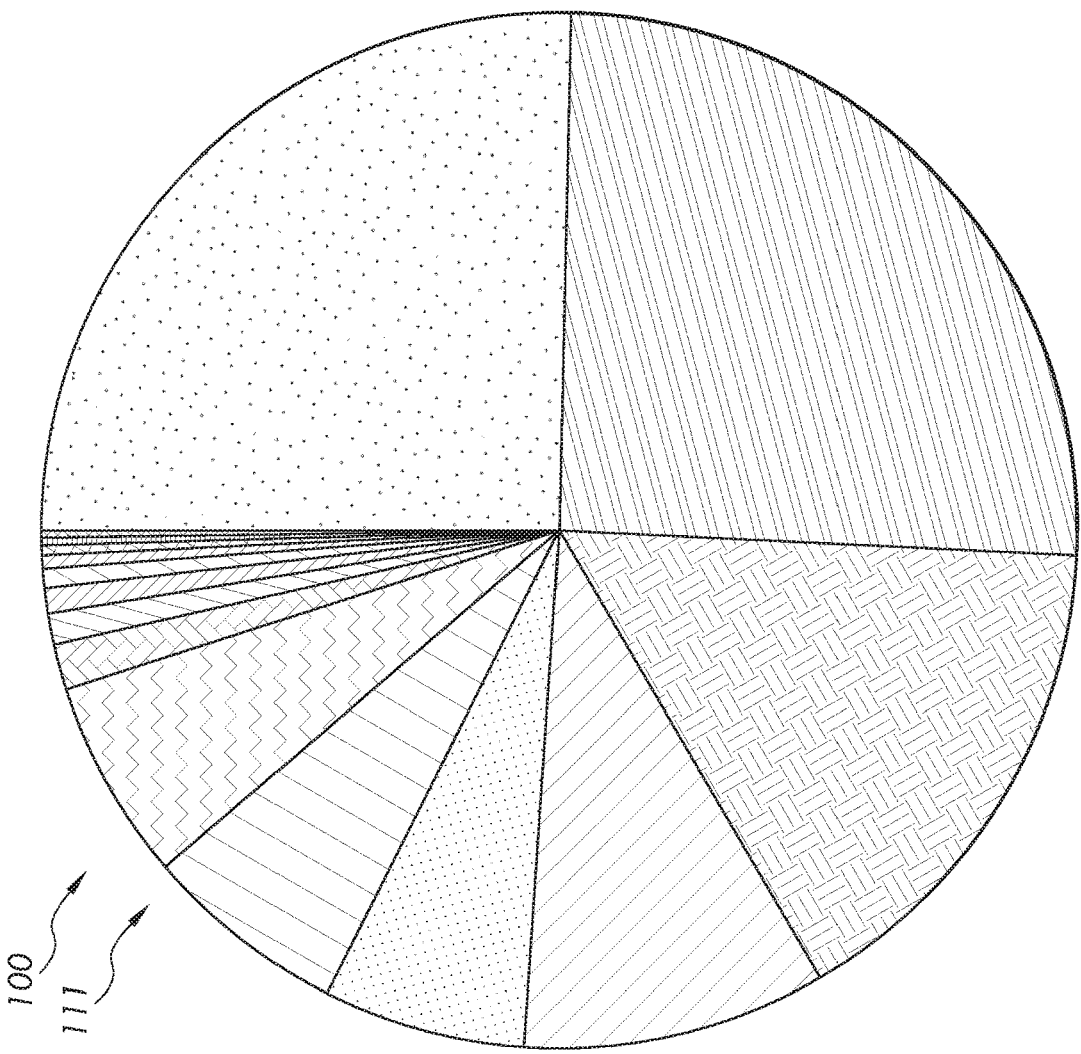
FIG. 1 is a pie chart illustrating volumetric ratios of a group of constituents forming a cream composition for massage and sport, according to one embodiment of the present disclosure.

As discussed above, embodiments of the present disclosure relate to topical creams, and more particularly to a massage and sport cream composition as used to assist with comforting muscular pain, increasing flexibility, comforting muscular pain, swelling, fatigue, cramps, increasing flexibility and mobility, easing joint pain and nerve pain, and improving overall skin condition.

Generally speaking, the massage and sport cream of the present disclosure is designed to be used for all massage types as a massage cream, especially by people who suffer discomfort from autoimmune disease such as multiple sclerosis, scleroderma, cerebral palsy, arthritis, Parkinson disease, epilepsy and other physical therapy cases. The compositions are administered topically, generally by massaging the compositions into the skin of the affected area(s). This makes it a great, pleasant cream to use in both homes and physical therapy treatment centers. Preliminary uses suggest that the massage and sport cream also can be used in sports massages for athletes in a spray form in the sports field, for instance during any sudden muscle cramp, muscle stiffness, joint or back pain, and swelling. The special and unique qualities and stem cell qualities of the organic essential oils mixed in this cream make it a special composition not like any other typical massage cream on the market.

In addition to having significant comfort properties, the massage and sport cream has also been used to increase flexibility, relieve tension, and improve skin conditions in the areas applied. The cream may further help with skin qualities and condition after consistent use, for example with stretch mark size, color, and texture. Generally the effect of the cream may be noticed approximately 40 minutes after application. Application may involve massaging the affected area thoroughly for at least 10 minutes. Additionally, the massage and sport cream composition has been found to be beneficial when used by people who suffered from muscular and autoimmune diseases. Additional benefits have been seen in the areas of muscular flexibility, pain reduction, and decreased muscle cramps in users who have sciatic pain, back pain, joint pain, and acute nerve pain. Further, the massage and sport cream may be used in physical therapy centers and in sports medicine cases to help with various muscular issues.

The massage and sport cream of this present disclosure is unique due to its organic essential oil mix and stem cell oil qualities. These ingredients have the capabilities to penetrate deep into the skin for targeted results.

Referring now more specifically to the drawings by numerals of reference, there is shown in FIGS. 1-4, various views of a massage and sport cream composition system 100. Here, the massage and sport cream composition system 100 may be beneficial for use by a user 140 to assist with treating muscular pain, increasing flexibility, and improving overall skin health. In a preferred embodiment of the present system, a topically-applied cream composition 111 is provided.

In reference to FIG. 1, there is a pie chart illustrating a preferred formulation of cream composition 111 embodying the present massage and sport cream composition system 100. The cream composition 111 is preferably formulated from ricinus communis (castor) seeds oil, sesamum indicum (sesame) seeds oil, deionized water, isopropyl myristate, triticum vulgare (wheat) germ oil, butyrospermum parkii (shea) butter, white iodine, cetostearyl alcohol, a fragrance, sodium laureth sulfate (SLES), bentonite, dmdm hydantoin, sodium chloride, benzyl alcohol, and behydroacetic acid.

Referring now to the beneficial properties of some ingredients formulated in the cream composition 111, it has been shown that sesame oil contains very important minerals that can play a big role in supporting nerves and bone density. These minerals may include: manganese, copper, calcium, iron, magnesium, tryptophan, zinc, fiber, thiamin, vitamin B6, phosphorous, and protein. When used on the nerves under the muscles, sesame oil has been proven to decrease IFN-gamma secretion, a key actor in autoimmune inflammation and injury in the nervous system. Sesame oil can also help in relieving muscle pain and swelling, enhancing blood circulation, allowing for proper elimination of toxins, supporting and fortifying the immune system, helping relaxation, reducing insomnia, and improving physical stamina and virility.

The cream composition 111 also contains ricinus communis (castor) seeds oil which may help the lymphatic nodes under the skin by increasing circulation of the lymphatic flow, prevent the growth of bacteria, yeast, and mold thereby reducing viruses, skin disorders, itching, and swelling of the skin. It has been suggested that castor oil may help in lymphatic congestion which is a major factor leading to inflammation and disease. Castor seeds contain a high concentration of a special fatty acid called ricinoleic acid which is believed to help with healing properties of the body. Castor oil has further been reported to help improve some symptoms and conditions associated with autoimmune diseases such as multiple sclerosis, scleroderma, arthritis, cerebral palsy, and epilepsy. In addition, castor oil may help in preventing the formation and expansion of stretch marks in the skin.

Another ingredient contained in the cream composition 111 is triticum vulgare (wheat) germ oil. This oil contains fatty acids that have been proven to help the muscular, cardio vascular, and central nervous systems by increasing the optimal storage of glycogen in the muscles. This in turn may help to promote muscle coordination, improve muscle growth, and increase endurance through reduced fatigue. Wheat germ oil is a rich source of vitamin B6, folic acid of the Vitamin B complex, magnesium, potassium, and phosphorus along with many other essential nutrients. Wheat germ oil contains vitamin B, which may help in repairing tissue damage and in tissue growth. It also helps other minerals, vitamins and nutrients reach the cells of the body. Wheat germ oil is high in a long chain, saturated, primary alcohol called octacosanol that improves the muscular energy. Thus, wheat germ oil is highly recommended for people who play sports. It delivers energy and oxygen during exercise along with increasing energy. Wheat germ oil also helps in promoting healthy skin as it prevents many skin problems like psoriasis, eczema, and dry skin.

The cream composition 111 may also include butyrospermum parkii (shea) butter which is rich in stearic, oleic acids, vitamin E, and vitamin A The vitamin A in shea butter is important for improving a number of skins conditions including blemishes, wrinkles, eczema, and dermatitis. Additionally, premium shea butter cream has properties used to treat skin allergies, insect bites, sunburns, frostbites, and a number of other conditions. Shea butter has be demonstrated to have unparalleled moisturizing properties due to several natural moisturizers present in the cream itself.

These are just a few of the benefits associated with the main ingredients contained in the cream composition 111 of the present massage and sport cream composition system 100. Although the exact mechanism of operation remains unclear, it is possible that a synergistic interaction between the complex oils of the claimed composition functions to enhance or magnify one or more of the analgesic, muscle relieving, and skin enhancing properties of the constituents. Further, it is possible that the synergistic interaction between the complex oils functions to produce a bio-affecting and body treating composition. Regardless of the actual mechanism, the beneficial properties of the present system appear to be unprecedented in the prior art.

FIG. 1 further illustrates preferred volumetric ratios of the ingredients forming the cream composition 111. In such a preferred composition, approximately 25% of the volume of the composition is the ricinus communis (castor) seeds oil, approximately 25% of the volume is the sesamum indicum (sesame) seeds oil, approximately 16% of the volume is the deionized water, approximately 10% of the volume is the isopropyl myristate, approximately 6% of the volume is the triticum vulgare (wheat) germ oil, approximately 6% of the volume is the butyrospermum parkii (shea) butter, approximately 6% of the volume is the white iodine, approximately 1% of the volume is the cetostearyl alcohol, approximately 1% of the volume is the fragrance, approximately 1% of the volume is the sodium laureth sulfate (SLES), approximately 1% of the volume is the bentonite. The dmdm hydantoin, the sodium chloride, the benzyl alcohol, and the behydroacetic acid each further constitute less than 1% of the composition's volume.

Figure 2:
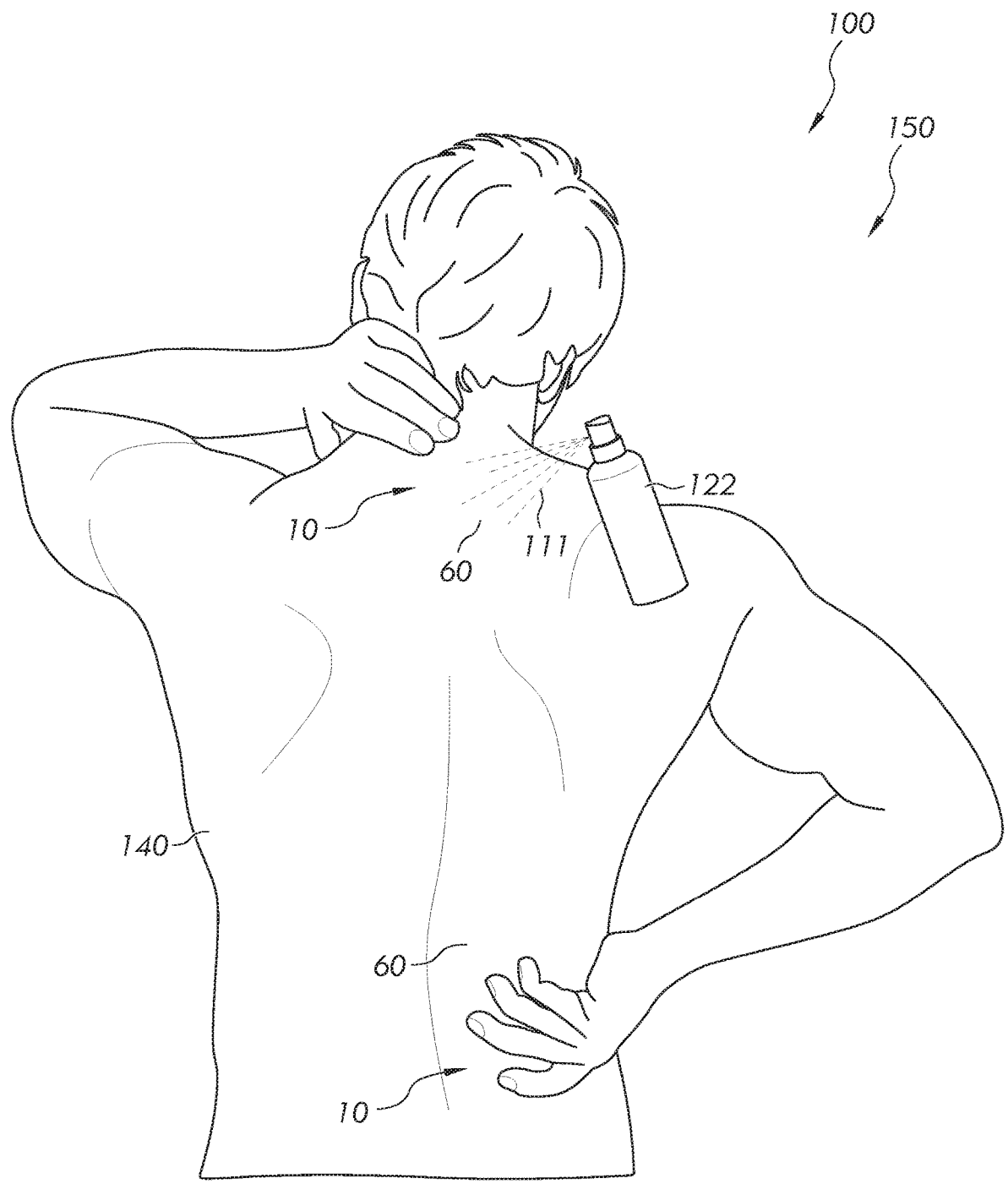
FIG. 2 is a perspective view, illustrating a topical application of the cream composition for massage and sport to a pain-affected body region of a user, according to one embodiment of the disclosure.

FIG. 2 is a perspective view illustrating the massage and sport cream composition system 100 of FIG. 1 during an 'in-use' condition 150, according to an embodiment of the present disclosure. Shown here is the topical application of the cream composition 111 to a representative pain-affected body region 10 of the user 140. The user 140 may apply the cream composition 111 topically to the skin surrounding the pain-affected body region 10 by using a cream dispenser such as dispensing container 122. In particular, the dispensing container 122 may be configured to carry and to dispense or otherwise deliver the cream composition 111 to a region of interest such that the user 140 can then massage it in by hand. This may be performed externally in various areas where there may be nerve or muscle pain 60 below the skin. Advantageously, the cream composition 111 may generally begin to deliver maximum effect to associated discomfort within 40 minutes from an application.

Figure 3:
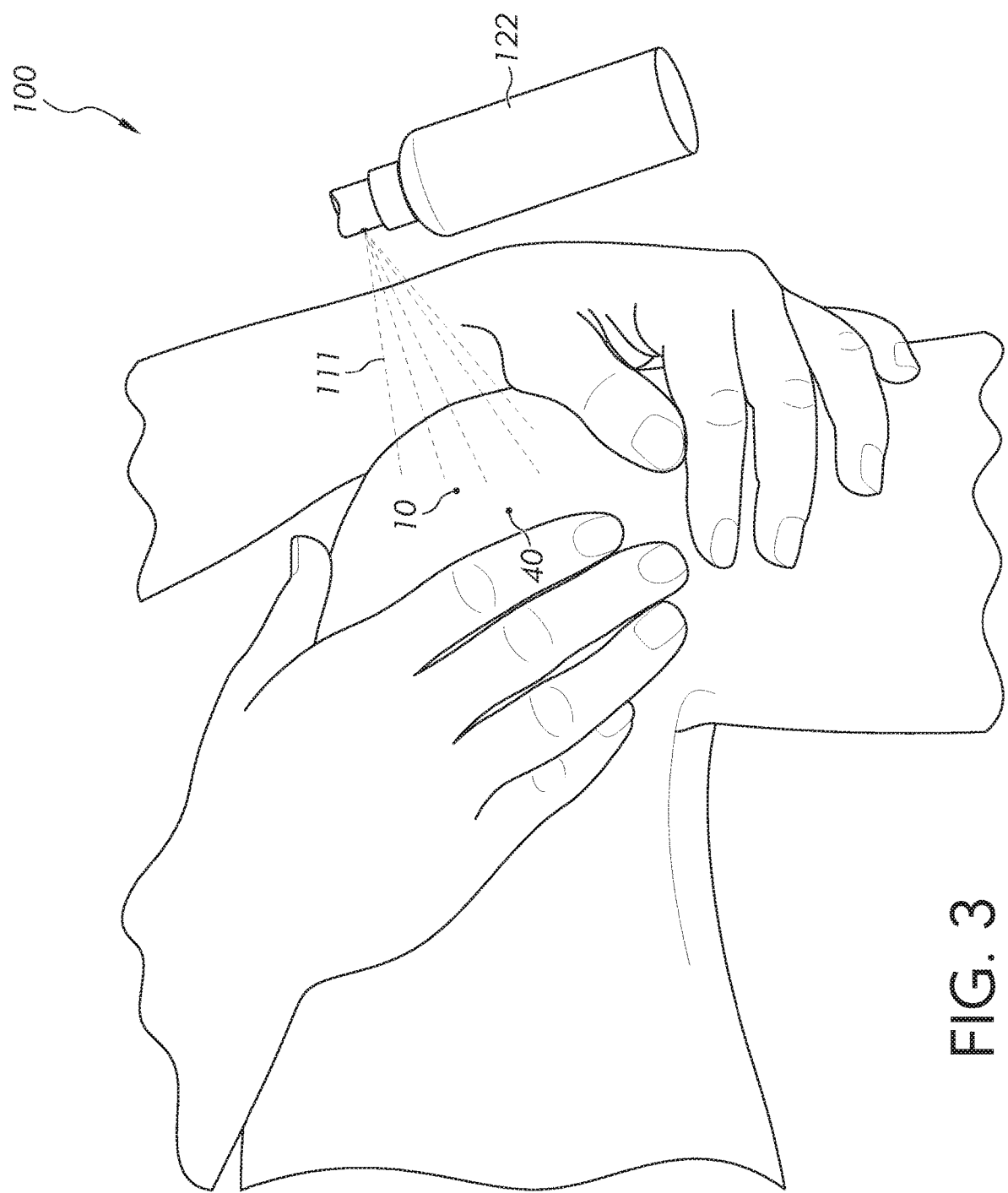
FIG. 3 is a perspective view, illustrating a topical application of the cream composition for massage and sport to a knee of a user, according to one embodiment of the disclosure.

FIG. 3 is a perspective view, illustrating the topical application of the cream composition 111 of a massage and sport cream composition system 100 to a joint 40 of the user 140, according to the preferred embodiment of FIG. 1. For joint pain relief or comfort, a predefined dose of the cream composition 111 may be applied to the discomforted or pain-affected body region 10 of the user 140 by use of the dispensing container 122 and then massaged in by hand until thoroughly absorbed into the skin, as shown. Additional treatments may be applied by the user as prescribed on a daily basis for maximum therapeutic relief and reconditioning of the pain-affected body region 10.

Figure 4:
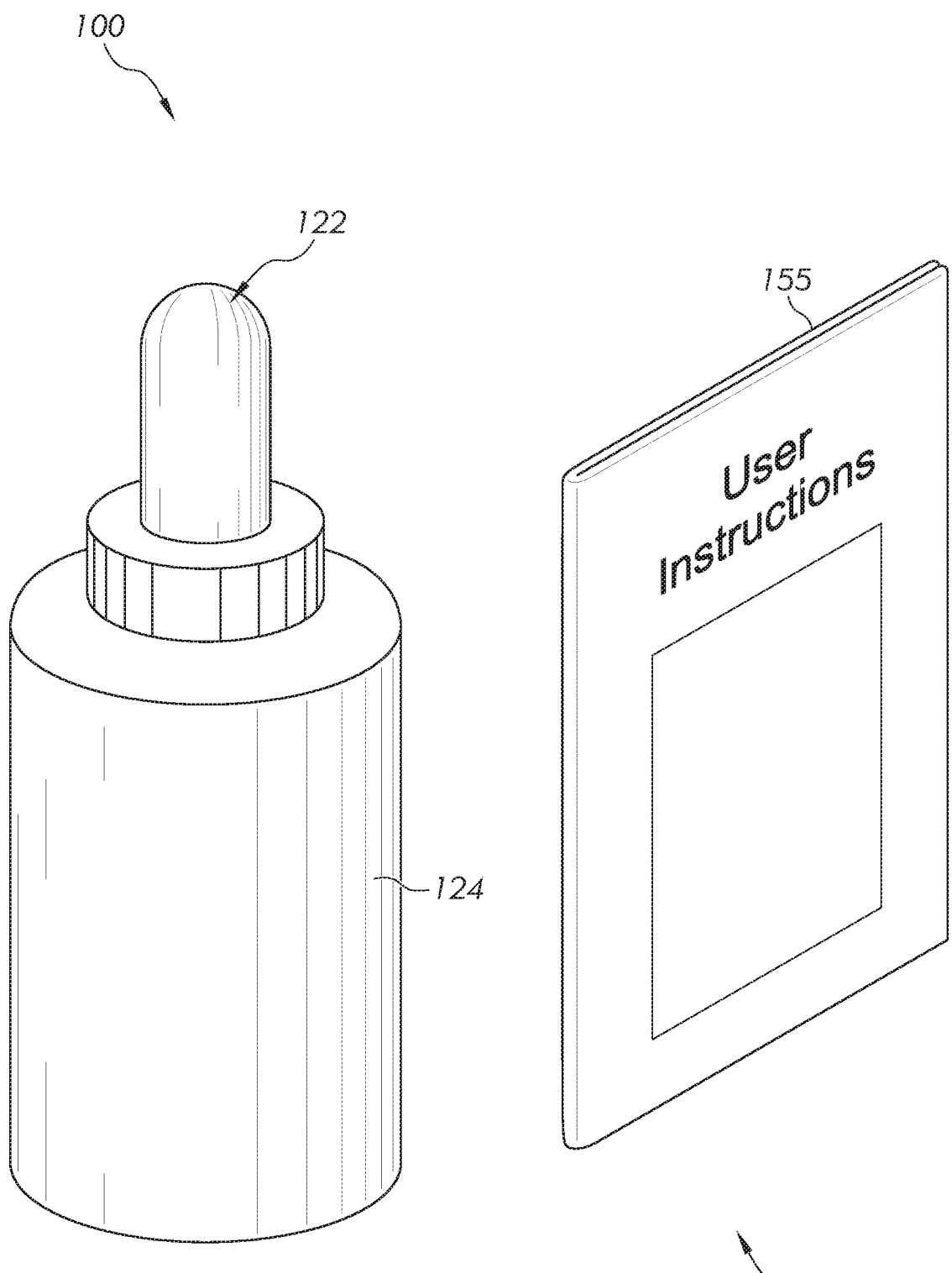
FIG. 4 is a perspective view, illustrating a kit including the cream composition for massage and sport, according to another embodiment of the present disclosure.

FIG. 4 is a perspective view, illustrating a kit 105 including the cream composition 111 (FIG. 1), according to another preferred embodiment of the present system. Massage and sport cream composition systems 100 may be sold as a kit 105 including the following parts: at least one dispensing container 122 configured to hold and dispense a quantity of the cream composition 111 and at least one set of user instructions 155. The kit 105 has instructions 155 such that functional relationships are detailed in relation to the composition of the embodiment (such that the system can be used, maintained, or the like in a preferred manner). The kit 105 may further include a cream reservoir 124 that is configured to carry an amount of the cream composition 111 additional in addition to the dispensing container 122. The cream reservoir 124 may be further configured to supply and resupply the dispensing container 122. According to one embodiment, the dispensing container 122 may be integrated with cream reservoir 124 such that cream reservoir 124 forms a removable part (e.g., via threaded interface) of the dispensing container 122.

The massage and sport cream composition system 100 may be supplied for sale in a wide variety of volumes, containers, and quantities for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized applicators, different dispenser combinations, parts may be sold separately, etc., may be sufficient.

The embodiments of the disclosure described herein are exemplary and numerous modifications, variations and rearrangements can be readily envisioned to achieve substantially equivalent results, all of which are intended to be embraced within the spirit and scope of the disclosure. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

The invention claimed is:

1. A method for treating muscular pain, cramps and tension in humans in need thereof consisting essentially of:
   mixing and creaming ricinus communis seed oil, sesamum indium seed oil, deionized water, isopropyl myristate, triticum vulgare germ oil, butyrospermum parkii butter, white iodine, cetostearyl alcohol, sodium laureth sulfate, bentonite, dmdm hydantoin, sodium chloride, benzyl alcohol, and
   behydroacetic acid, wherein:
   approximately 25% of the volume of the composition is the ricinus communis seed oil,
   approximately 25% of the volume of the composition is the sesamum indicum seed oil,
   approximately 16% of the volume of the composition is the deionized water,
   approximately 10% of the volume of the composition is the isopropyl myristate,
   approximately 6% of the volume of the composition is the triticum vulgare germ oil, approximately 6% of the volume of the composition is the butyrospermum parkii butter, approximately 6% of the volume of the composition is the white iodine, approximately 1% of the volume of the composition is the cetostearyl alcohol, approximately 1% of the volume of the composition is the sodium laureth sulfate, approximately 1% of the volume of the composition is the bentonite, and wherein the dmdm hydantoin, the sodium chloride, the benzyl alcohol, and the behydroacetic acid each constitute less than 1% of the composition's volume but not 0%; and wherein the composition is applied topically to the human in need thereof and wherein the composition effectively treats muscular pain, cramps and tension in the human in need thereof.

* * * * *